US008841130B2

(12) United States Patent
Goldman

(10) Patent No.: US 8,841,130 B2
(45) Date of Patent: Sep. 23, 2014

(54) METHODS AND KIT FOR ENDOMETRIOSIS DIAGNOSIS

(75) Inventor: Dorothee Goldman, Hammondsport, NY (US)

(73) Assignee: Oratel Diagnostics, LLC, Hammondsport, NY (US)

( * ) Notice: Subject to any disclaimer, the term of this patent is extended or adjusted under 35 U.S.C. 154(b) by 0 days.

(21) Appl. No.: 13/546,280

(22) Filed: Jul. 11, 2012

(65) Prior Publication Data

US 2013/0017614 A1 Jan. 17, 2013

Related U.S. Application Data

(60) Provisional application No. 61/506,262, filed on Jul. 11, 2011, provisional application No. 61/538,192, filed on Sep. 23, 2011.

(51) Int. Cl.
*G01N 33/48* (2006.01)
*G01N 21/78* (2006.01)
*G01N 21/82* (2006.01)

(52) U.S. Cl.
USPC ................ 436/63; 436/93; 436/103; 436/164

(58) Field of Classification Search
CPC ....... G01N 21/75; G01N 21/78; G01N 21/82; G01N 33/48; G01N 33/52
USPC ........................ 436/63, 86, 103, 93, 164, 166
See application file for complete search history.

(56) References Cited

U.S. PATENT DOCUMENTS

| | | |
|---|---|---|
| 4,358,288 A | 11/1982 | Goldman |
| 5,334,502 A | 8/1994 | Sangha |
| 5,356,817 A | 10/1994 | Cole |
| 5,922,613 A | 7/1999 | Goldman |
| 5,981,291 A | 11/1999 | Goldman |
| 6,294,349 B1 | 9/2001 | Streckfus |
| 6,531,277 B2 | 3/2003 | Timms |
| 6,645,725 B2 | 11/2003 | Yeaman |
| 6,780,594 B2 | 8/2004 | Hess-Stumpp et al. |
| 6,867,051 B1 | 3/2005 | Anderson et al. |
| 6,972,180 B1 | 12/2005 | Streckfus et al. |
| 8,420,398 B2 * | 4/2013 | Goldman ........................ 436/65 |
| 2003/0166014 A1 | 9/2003 | Timms |
| 2005/0220912 A1 | 10/2005 | Theoharides |
| 2005/0240085 A1 | 10/2005 | Knoell et al. |
| 2006/0013905 A1 | 1/2006 | Tehoharides |
| 2008/0200379 A1 | 8/2008 | Tabibzadeh et al. |
| 2008/0241852 A1 | 10/2008 | Messer et al. |
| 2010/0267003 A1 | 10/2010 | Goldman |
| 2010/0272637 A1 | 10/2010 | Schilling |
| 2011/0015087 A1 | 1/2011 | Nagore Casas et al. |

FOREIGN PATENT DOCUMENTS

| | | | |
|---|---|---|---|
| WO | 96/29606 A1 | 9/1996 | |
| WO | 00/47739 A2 | 8/2000 | |
| WO | 2007/126982 A1 | 11/2007 | |

OTHER PUBLICATIONS

International Search Report, International Application No. PCT/US2012/046175, mailed Oct. 5, 2012, 4pp.
E. Attar et al, "Aromatase and other steroidogenic genes in endometriosis: translational aspects", Human Reproduction Update, 2006, pp. 49-56, vol. 12 No. 1.
T. Ediger et al, "Estrogen Receptor Regulation of the Na+/H+ Exchanger Regulatory Factor", Endocrinology, 2009, pp. 2976-2982, vol. 140 No. 7.
L. Sevon et al, "Effect of Age on Flow-Rate, Protein and Electrolyte Composition of Stimulated Whole Saliva in Healthy, Non-Smoking Women", The Open Dentistry Journal, 2008, pp. 89-92.
L.C. Kao et al, "Expression Profiling of Endometrium from Women with Endometriosis Reveals Candidate Genes for Disease-Based Implantation Failure and Infertility", Endocrinology, 2003, pp. 2870-2881, vol. 144 No. 7.
S. Parkkila et al, "Immunohistochemical Localization of Carbonic Anhydrase Isoenzymes VI, II and I in Human Parotid and Submandibular Glands", The Journal of Histochemistry and Cytochemistry, 1990, pp. 941-947,vol. 38 No. 7.
E. Szmuilowicz et al, "Relationship between Aldosterone and Progesterone in the Human Menstrual Cycle", The Journal of Endocrinology & Metabolism, 2006, pp. 3981-3987, vol. 91 No. 10.
C.A.B. Clemetson et al, "The Effects of Oestrogen and Progesterone on the Sodium and Potassium Concentrations of Rat Uterine Fluid", Journal of Endocrinology, 1970, pp. 309-319, vol. 47, 1 page Abstract.
S. Bulun et al, "Endometriosis", New England Journal of Medicine, Jan. 15, 2009, pp. 268-279, vol. 360 No. 3.
Research Projects, "Theory and modelling", 6 pages.
C. Hannig et al, "Transaminases in the acquired pellicle", Archives of Oral Biology, May 2009, pp. 445-448, vol. 54 No. 5, 2 page Abstract.
G. Fia et al, "Prediction of grape polyphenol astringency by means of a fluorimetric micro-plate assay", Food Chemistry, Mar. 2009, pp. 325-330, vol. 113 No. 1, 2 page Abstract.

(Continued)

*Primary Examiner* — Maureen Wallenhorst
(74) *Attorney, Agent, or Firm* — Berenato & White, LLC

(57) ABSTRACT

An endometriosis diagnostic in which a biological sample of a female mammal having had a menstrual cycle within 90 days of the biological sample having been obtained from the female mammal is subjected to an in vitro diagnostic procedure in which the biological sample is contacted with an apatite compound for an effective time to provide a responsive visual appearance. Based on the visual appearance, a determination is made whether the female mammal has endometriosis.

16 Claims, No Drawings

(56) References Cited

OTHER PUBLICATIONS

R.M. Nagler et al, "Salivary glands and the aging process: mechanistic aspects, health-status and medicinal-efficacy monitoring", Biogerontology, 2004, pp. 223-233, vol. 5, 1 page Abstract.
N. Stachenfeld et al, "Progesterone increases plasma volume independent of estradiol", Journal of Applied Physiology, 2005, pp. 1991-1997, vol. 98.
"Saliva may paint an insightful view of the body's health", Jun. 12, 2005, http://www.medilexicon.com/medicalnews.php?newsid=26004.
D. Goldman, "A discussion about pH patterns and absorbency patterns for malividin 3,5 digluocside mixed with saliva samples from a woman with endometriosis and a woman who does not have endometriosis and a comparison of estradiol levels in saliva to pH patterns and to optical density patterns", Mar. 20, 2006, 14 pages.
Bedaiwy et al, "Prediction of endometriosis with serum and peritoneal fluid markers: a prospective controlled trial", Human Reproduction, 2002, pp. 426-431, vol. 17 No. 2.
Koshiba et al, "Expression of Allograft Inflammatory Factor-1 in Human Eutopic Endometrium and Endometriosis: Possible Association with Progression of Endometriosis", The Journal of Clinical Endocrinology & Metabolism, 2005, pp. 529-537, vol. 90 No. 1.
H. Valimaa et al, "Estrogen receptor-beta is the predominant estrogen receptor subtype in human oral epithelium and salivary glands", Journal of Endocrinology, 2004, pp. 55-62, vol. 180.
Ja-Mun Chong et al, "Interleukin 1beta Expression in Human Gastric Carcinoma with Epstein-Barr Virus Infections", Journal of Virology, Jul. 2002, pp. 6825-6831, vol. 76, No. 13.
C. Ballare et al, "Two Domains of the Progesterone Receptor Interact with the Estrogen Receptor and Are Required for Progesterone Activation of the c-Src/Erk Pathway in Mammalian Cells", Molecular and Cellular Biology, Mar. 2003, pp. 1994-2008, vol. 23 No. 6.
M.E. Baker "Beyond Carrier Proteins Albumin, steroid hormones and the origin of vertebrates", Journal of Endocrinology, 2002, pp. 121-127, vol. 175.
S. Kavoussi et al, "Periodontal disesase and endometriosis: Analysis of the National Health and Nutrition Examination Survey", Fertility and Sterilility, Feb. 2009, pp. 335-342; vol. 91 No. 2.
J. Hu et al, "Carbonic Anhydrase Regulate Endometrial Gland Development in the Neonatal Uterus", Biology of Reproduction, 2005, pp. 131-138; vol. 73.
D. He et al, "Characterization of Proline-Serine-Rich Carboxyl Terminus in Human Sulfotransferase 2B1b: Immunogenicity, Subcellular Localization, Kinetic Properties, and Phosphorylation", Drug Metabolism and Disposition, pp. 1749-1755, vol. 34 No. 10, 2006.
M. C. Rose et al, "Respiratory Tract Mucin Genes and Mucin Glycoproteins in Health and Disease", Physiological Reviews, 2006, pp. 245-278, vol. 86.
G. Goobes et al, "Folding of the C-terminal bacterial binding domain in statherin upon adsorption onto hydroxyapatite crystals", PNAS, Oct. 31, 2006, pp. 16083-16088, vol. 103 No. 44.
N. Heldring et al, "Estrogen Receptors: How Do They Signal and What Are Their Targets", Physiological Reviews, 2007, pp. 905-931, vol. 87.
E. Azen, et al, "Genetic Polymorphism of Proline-Rich Human Salivary Proteins", Science, Jun. 8, 1973, pp. 1067-1069; vol. 180 No. 4090, 1 page Abstract.
S. Senapati et al, "Mucin-interacting proteins: from function to therapeutics", Trends in Biochemical Sciences, Apr. 2010, pp. 236-245, vol. 35 No. 4.
International Search Report, International Application No. PCT/US2007/007803, mailed Jun. 9, 2007, 4pp.
International Search Report, International Application No. PCT/US11/46586, mailed Mar. 8, 2012, 4pp.
S. Simoens, et al, "Endometriosis: cost estimates and methodological perspective", Hum Reprod Update, 2007, pp. 395-404, July-Aug, 13(4).
T. Price, et al, "Immunofluorescent Localization of a Novel Progesterone Receptor(s) in a T47D-Y Breast Cancer Cell Line Lacking Genomic Progesterone Receptor Expression", J Soc Gynecol Investig, Dec. 2005, pp. 610-616, vol. 12, No. 8.
B. Kay, et al, "The importance of being proline: the interaction of proline-rich motifs in signaling proteins with their cognate domains", The FASEB Journal, Feb. 2000, pp. 231-241, vol. 14.
V. Boonyaratanakornkit, et al, "Progesterone Receptor Contains a Proline-Rich Motif that Directly Interacts with SH3 Domains and Activates c-Src Family Tyrosine Kinases", Molecular Cell, Aug. 1, 2001, pp. 269-280, vol. 8.
G. Proctor, et al, "The Function of Salivary Proteins and the Regulation of Their Secretion by Salivary Glands", Biomed Rev, 1998, pp. 3-15, vol. 9.
P.G. Groothuis, et al, "Estrogen and the endometrium: lessons learned from gene expression profiling in rodents and human", Human Reproduction Update, 2007, pp. 405-417, vol. 13, No. 4.
K. Pettersson, et al, "Role of Estrogen Receptor Beta in Estrogen Action", Annual Review of Physiology, 2001, pp. 165-192, vol. 63.
P. Calias, et al, "Synthesis of inositol 2-phosphate-quercetin conjugates", Carbohydrate Research, 1996, pp. 83-90, vol. 292.
E. Markou, et al, "The Influence of Sex Steroid Hormones on Gingiva of Women", The Open Dentistry Journal, 2009, pp. 114-119, vol. 3.
G. Attia, et al, "Progesterone Receptor Isoform A But Not B Is Expressed in Endometriosis", The Journal of Clinical Endocrinology & Metabolism, 2000, pp. 2897-2902, vol. 85, No. 8.
J. Aplin, "MUC-1 glycosylation in endometrium: possible roles of the apical glycocalyx at implantation", Human Reproduction, 1999, pp. 17-25, vol. 14 (Suppl. 2).
S. Hild-Petito, "Mucin (Muc-1) Expression Is Differentially Regulated in Uterine Luminal and Glandular Epithelia of the Baboon (*Papio anubis*)"; Biology of Reproduction, 1996, pp. 939-947, vol. 54.
P. Sarni-Manchado, et al, "Influence of the Glycosylation of Human Salivary Proline-Rich Proteins on Their Interactions with Condensed Tannins" J. Agric. Food Chem., 2008, pp. 9563-9569, vol. 56.
A. Rodgers, et al, "Inhibition of CD44 N- and O-linked Glycosylation Decreases Endometrial Cell Lines Attachment to Peritoneal Mesothelial Cells", Fertil Steril., Feb. 2011, pp. 823-825, vol. 95, No. 2.
A. Van Nieuw Amerongen, et al, "Salivary Proteins: Protective and Diagnostic Value in Cariology?", Caries Research, 2004, pp. 247-253, vol. 38.
G.B. Proctor, et al, "Salivary Proteins Interact with Dietary Constituents to Modulate Tooth Staining", Journal of Dental Research, 2005, vol. 84, No. 1, 1 page Abstract.
H. Zhang, et al, "Use of proteomic analysis of endometriosis to identify different protein expression in patients with endometriosis versus normal controls", Fertility and Sterility, Aug. 2006, pp. 274-282, vol. 86, No. 2.
L. Margarit, et al, "MUC1 as a Discriminator between Endometrium from Fertile and Infertile Patients with PCOS and Endometriosis", J Clin Endocrinol Metab, Dec. 2010, pp. 5320-5329, vol. 95, No. 12.
A. Bennick, et al, "The Nature of the Hydroxyapatite-Binding Site in Salivary Acidic Proline-Rich Proteins", Biochem. J., 1979, pp. 115-126, vol. 183.
G. Madapallimattam, et al, "Phosphopeptides derived from human salivary acidic proline-rich proteins", Biochem. J., 1990, pp. 297-304, vol. 270.
B. Sengupta, et al, "The interaction of quercetin with human serum albumin: a fluorescence spectroscopic study", Biochemical and Biophysical Research Communications, 2002, pp. 400-403, vol. 299.
C. Dufour, et al, "Flavonoid-serum albumin complexation: determination of binding constants and bindling sites by fluorescence spectroscopy", Biochemical and biophysical research communications, 2002, vol. 299, No. 3, 1 page Abstract.
B. Delvoux, et al, "Increased Production of 17 beta-estradiol in Endometriosis Lesions Is the Result of Impaired Metabolism", J Clin Endocrinol Metab., Mar. 2009, pp. 876-883, vol. 94, No. 3.
M. Meseguer, et al, "MUC1 and endometrial receptivity", Molecular Human Reproduction, 1998, pp. 1089-1098, vol. 4, No. 12.
Byoung-Moo Seo, et al, "Investigation of multipotent postnatal stem cells from human periodontal ligament", The Lancet, Jul. 10, 2004, vol. 364, Issue 9429, 2 pp Summary.

(56) References Cited

OTHER PUBLICATIONS

H. Taylor, "Endometrial cells derived from donor stem cells in bone marrow transplant recipients", JAMA, 2004, vol. 292, No. 1, 2 pp Abstract.

K. Sakabe, et al, "Progestin and estrogen receptors: characterization and localization in rat submandibular glands, with special reference to epidermal growth factor", Endocrinol Jpn., Oct. 1988, vol. 35, No. 5, 1 pg. Abstract.

A. Zalewska, et al, "Structure and biosynthesis of human salivary mucins", Acta Biochimica Polonica, 2000, vol. 47, No. 4, pp. 1067-1079.

Gargett, "Uterine stem cells: What is the evidence?", Human Reproduction Update, 2007, pp. 87-101, vol. 13, No. 1.

J. Ai, et al, "Endometrial Stem Cells and Endometriosis", http://www.intechopen.com/books/endometriosis-basic-concepts-and-current-research-trends/endometrial-stem-cells-and-endometriosis, pp. 297-308.

Lori, et al, "Mechanism for the Adsorption of Mucin on Hydroxyapatite", Nigerian Journal of Chemical Research, 2005, pp. 21-29, vol. 10.

A. Fukushima, et al, "Role of Na+ and Ca2+ Channels in the Preoptic LH Surge Generating Mechanism in Proestrous Rats", Endocrine Journal, 2003, pp. 145-153, vol. 50, No. 2.

G. Proctor, et al, "The Function of Salivary Proteins and the Regulation of Their Secretion by Salivary Glands", Biomedical Reviews, 1998, pp. 3-15, vol. 9.

V. Braga, et al, "Modulation of Muc-1 mucin expression in the mouse uterus during the estrus cycle, early pregnancy and placentation", Journal of Cell Science, 1993, pp. 397-405, vol. 105.

B, Madhan, et al, "A Semi-Empirical Quantum Mechanical Modeling Study on the Interaction of Collagen-like Peptides with Polyphenolic Molecules: An Attempt to Gain Insights into Vegetable Tanning", JALCA, 2003, pp. 272-277, vol. 98.

S. Chiappin, et al., "Saliva specimen: A new laboratory tool for diagnostic and basic investigation", Clinica Chimica Acta 383, 2007, pp. 30-40.

Wettemann, et al., "Estradiol and Progesterone in Blood Serum during the Bovine Estrous Cycle", Journal of Animal Science, Jan. 1, 1972, pp. 1020-1024, vol. 34, No. 6.

Firk, et al., "Automation of oestrus detection in dairy cows: a review", Livestock Production Science, Jul. 1, 2002, pp. 219-232, vol. 75, No. 3.

Senger, "The Estrus Detection Problem: New Concepts, Technologies, and Possibilities", Journal of Dairy Science, American Dairy Science Association, Sep. 1, 1994, pp. 2745-2753, vol. 77, No. 9.

Liu et al, "Growth of Highly Oriented Hydroxyapatite Arrays Tuned by Quercetin", Chemistry—A European Journal, Apr. 27, 2012, pp. 5519-5523, vol. 18 Issue 18.

\* cited by examiner

METHODS AND KIT FOR ENDOMETRIOSIS DIAGNOSIS

CLAIMS OF PRIORITY AND CROSS-REFERENCES TO RELATED APPLICATIONS

This application claims the benefit of priority of U.S. Provisional Application Nos. 61/506,262 filed Jul. 11, 2011 and 61/538,192 filed Sep. 23, 2011, the complete disclosures of which are incorporated herein by reference.

FIELD OF THE INVENTION

The present invention is directed to improved and reliable methods, systems, and kits for endometriosis diagnosis. In exemplary embodiments of the invention, diagnosis is performed on a biological sample obtained in a non-invasive manner, and the systems, methods, and kits allow for early and reliable diagnosis of endometriosis.

BACKGROUND OF THE INVENTION

Endometriosis has been classified as an immune deficiency disease ("Pathogenesis of Endometriosis: Natural Immunity Dysfunction or Autoimmune Disease," *Trends Mol Med.*, 9(5):223-8, May 2003, G. Matarase, G. De Placido, Y. Nikas, C. Alviggi) that affects approximately seven (7) percent of the pre-menopausal women worldwide in their reproductive years and accounts for twenty-three (23) percent of female fertility issues (www.mindbranch.com/products). The annual healthcare costs and costs of productivity loss associated with endometriosis were estimated as $22 billion for 2002. *Endometriosis: cost estimates and methodological perspective*, Hum. Reprod. Update (2007) 13(4):395-404, S. Simoens, L. Hummelshoj, T. D'Hooghe.

Endometriosis is characterized by ectopic lesions of endometrial tissue in various organs of the body outside the uterine cavity. Harvard Medical School Family Health Guide (1999) 1071, A. Komaroff. Ectopic lesions of endometrial tissue are typically found on the ovaries, fallopian tubes, ligaments that support the uterus, areas around the vagina and uterus, and areas within the peritoneal and pelvic cavities. The ectopic lesions form benign tumors on organs which can lead to inflammation, severe discomfort and pelvic pain, and reproductive failure. (www.coobgyn.com/pt/re/coobgyn/abstract)

The ectopic endometrial lesions are similar to endometrial tissue which lines the uterus. Unlike endometrial tissue lining the uterus, however, ectopic endometrial lesions are unable to discharge from the body during menstruation. Internal bleeding results from the ectopic endometrial lesions, leading to the development of inflammation and scar tissue. One theory is that the ectopic lesions are thought to result from transport of endometriotic stem cells present in menstrual flow. *Uterine stem cells: what is the evidence*, Human Reproduction Update (2007), 13(1):87-101, C. E. Gargett. The stem cells can implant in other tissues that have growth factors and steroid hormone receptors which facilitate growth and development of blood vessels, nerves, and tissue within the implanted endometriotic tumors. Endometriotic tumors that develop in the pelvic cavity and the fallopian tubes are known to have steroid receptors and other growth factors that can facilitate growth and development of these misplaced endometriotic stem cells. Endometrial Stem Cells and Endometriosis, Jafar Ai and Esmaeil Sadroddiny Endometriosis—Basic Concepts and Current Research Trends, Department of Tissue Engineering, School of Advanced Medical Technologies, Tehran University of Medical Sciences, Tehran, Iran.

Endometriosis presents difficulties in diagnosis. The typical problems of pelvic pain and infertility are non-specific. Although endometriosis is one of the leading causes of infertility in women, it is estimated that less than half of women with endometriosis suffer from fertility problems. (www.healthywomen.org/healthtopics/endometriosis/q/L2/24/L1/3//) While the above-discussed increased sensitivity brought about by inflammation, scar tissue, and nerve tissue growth manifests as discomfort or severe pain, not all women afflicted with endometriosis experience the severe pain, and oftentimes severe pelvic pain can be attributed to causes other than endometriosis. (www.healthywomen.org/healthtopics/endometriosis/q/L2/24/L1//) Other symptoms of endometriosis may include diarrhea, intestinal pain, painful intercourse, abdominal tenderness, cramping, back ache, menstrual cramps, and excessive menstrual bleeding. These symptoms are not universally experienced throughout the population of females having endometriosis, and can be brought about by other illnesses and conditions such as fibroids and cysts.

The only accepted method for diagnosing endometriosis is laparoscopy of the pelvic cavity. However, laparoscopy is costly, invasive, and generally cannot be carried out without a trained specialist and expensive equipment. The high cost, inconvenience, and physical risks associated with laparoscopy can cause women to delay or decide against screening until symptoms become severe. Many attempts have been made to introduce simple non-invasive diagnostics for endometriosis. However, so far no method has been able to accurately diagnose endometriosis with as high of a degree of sensitivity or specificity than what has been documented with laparoscopy.

Many types of biomarkers such as CA-125, Tumor Necrosis Factor TNFα, CA19-9, E-cadherin, TIMP1, or MMP2, or autoimmune factors such as Il-8 known to be in elevated concentrations in women with endometriosis have been evaluated as potential serum markers for endometriosis. However, these markers are also elevated in certain cancers and are not specific to endometriosis. Furthermore, the markers are serum based and require regulated laboratory conditions for testing specimens.

A simple, low cost, non-invasive diagnostic that can test a biological sample of a female directly in the doctor's office, and preferably at home, for endometriosis would offer significant medical benefits towards promoting early detection diagnosis, decreasing medical costs associated with diagnosis and treatment, and enhancing valid population-based research.

SUMMARY

In accordance with a first aspect of the invention, an endometriosis diagnostic method is provided. A biological sample having been obtained from a female mammal within 90 days of a menstrual cycle of the female mammal is subjected to an in vitro diagnostic procedure which includes contacting the biological sample with an apatite compound for an effective time to provide a responsive visual appearance. Based on the responsive visual appearance and whether or not the female mammal experienced a luteinizing hormone surge in the menstrual cycle at the time that the biological sample was obtained, a determination is made whether the female mammal has endometriosis.

A second aspect of the invention provides an endometriosis diagnostic method in which a biological sample obtained from a female mammal during the luteal phase of a menstrual cycle is subjected to an in vitro diagnostic procedure which includes contacting the biological sample with an apatite compound, a flavonol, and an anthocyanin for an effective time to produce a color response. A determination is made whether the female mammal has endometriosis based on the color response.

A third aspect of the invention provides an endometriosis diagnostic method including in vitro contacting a biological sample obtained from a female mammal within 90 days of the mammal's cycle to an apatite compound to produce a visual response and determining whether the female mammal has endometriosis based on the visual response.

Other aspects of the invention, including other methods, devices, indicators, kits, and the like which constitute part of the invention, will become more apparent upon reading the following detailed description of the exemplary embodiments.

DETAILED DESCRIPTION OF EXEMPLARY EMBODIMENTS

Reference will now be made in detail to exemplary embodiments of the invention. It should be noted, however, that the invention in its broader aspects is not necessarily limited to the specific details, representative materials and methods, and illustrative examples described in connection with the exemplary embodiments and methods.

According to an exemplary embodiment of the invention, an endometriosis diagnostic method is provided. The diagnostic method is performed on a biological sample obtained from a female mammal who has had a menstrual cycle within the past 90 days. The female mammal desirably is within her child bearing years, is not pregnant, and is not post-menopause.

The selected biological sample preferably yet optionally is considered a non-invasive medium that is attainable from the subject without requiring penetration of the skin, such as with a needle or scalpel as part of a surgical procedure. Vaginal fluid, buccal mucosa, and saliva are particularly useful biological samples that may be utilized in exemplary embodiments of the invention for diagnosis of endometriosis. Saliva is desirable as a diagnostic biological fluid from a practical standpoint because of the non-invasive manner by which it may be obtained. The female mammal may provide whole non-stimulated saliva by, for example, drooling into a receptacle for 5 minutes. Alternatively, the saliva may be obtained by placing a swab into the mouth of the female mammal. The saliva sample is preferably 40 microliters or more.

While saliva is specified in connection with several exemplary embodiments and examples described herein, other bodily fluids and tissue, such as vaginal fluids, epithelial cells, blood, sweat, or fluids from mucosa, etc., possessing markers that allow for like testing procedures to be carried out may be selected.

The biological sample is contacted with an apatite compound as part of an in vitro diagnostic procedure. The apatite compound may be coated on a surface of a solid substrate such as glass or plastic or other polymer. An exemplary commercially available calcium phosphate apatite product is a multi-well surface assay plate coated with hydroxyapatite such as Osteo Assay Surface, CLS 3988 Sigma, distributed by Sigma Aldrich or Corning, Inc. The exemplary hydroxyapatite assay plate is described in Corning, Inc. marketing materials as mimicking in vivo bone for in vitro bone cell assays.

By way of example, eighty (80) microliters of the sample of whole non-stimulated saliva are pipetted onto the surface of a titer well such as Corning Osteo CLS 3988 titer plate that holds the hydroxyapatite.

The contact between the biological sample and hydroxyapatite is maintained for an effective time to provide a visual appearance of either clear or cloudy turbidity. The responsive visual appearance of either clear or cloudy turbidity typically can be determined within an hour, typically after approximately ten minutes, of contacting the biological sample to hydroxyapatite which has been applied to a solid surface such as plastic in a titer well or a glass slide. It is recommended not to mix or shake the biological sample with the apatite compound. The pH of the assay is preferably above 5 and is not changed significantly from the original pH of the biological sample obtained from the female mammal. Human saliva typically has a pH above 6 and below about 8, more specifically about 6.2 to about 7.4.

Evaluation of whether the sample is clear or opaque to the unaided human eye can be made by placing standard newsprint under surface that holds the treated sample. If the treated sample is transparent enough to permit reading of the newsprint through the treated sample, then the sample is considered clear and correlates to a female not having endometriosis. On the other hand, if the newsprint placed under the assay is not legible there through due to its opaqueness or cloudiness, then the sample is considered to have originated from a female mammal with endometriosis. Alternatively, evaluation of whether the sample is clear or opaque may be made with a spectrophotometer or plate reader set at, for example, 600 nm to measure light transmission. High optical density readings correlated to opaque responses while low optical density readings correlate to clear responses.

As a general rule, saliva protein complexes that are specific to women with endometriosis are believed to have high degrees of deglycosylation, which is believed to cause the complexes to aggregate towards the apatite compound, e.g., hydroxyapatite ($Ca_{10}(PO_4)_6(OH)_2$). If sufficient aggregation results, the protein complex will precipitate out and appear opaque (such as "cloudy") to the unaided human eye. On the other hand, hydroxyapatite-treated biological samples from women that do not have endometriosis will not form precipitates and will remain transparent. It is believed that the absence of significant precipitation is due to the high degree of glycosylation of the saliva protein complexes. That is, under this general rule the hydroxyapatite allows differentiation between biological samples of female mammals with endometriosis and female mammals without endometriosis, specifically providing an opaque turbidity response for female mammals with endometriosis and a transparent turbidity response for female mammals without endometriosis.

The exception to this general rule is where the biological sample is obtained from the female mammal at a point in the menstrual cycle corresponding to a surge in luteinizing hormone (LH). The LH surge takes place about 24 to about 36 hours before ovulation. Women not having endometriosis who have high LH values, as will occur at the time of ovulation, will have cloudy presentations for the hydroxyapatite assay, whereas women with endometriosis who have high LH levels will have clear results with the hydroxyapatite test. Estradiol levels are lowest and sodium levels are high during the LH surge. *A comparison of the ovulation method with the CUE ovulation predictor in determining the fertile period*, J. Am. Acad. Nurse Pract. (October 1996); 8(10):461-66, R. J. Fehring. Increased sodium and degylcosylation are believed to affect how the proteins respond to apatite compounds, e.g., hydroxyapatite ($Ca_{10}(PO_4)_6(OH)_2$. As discussed above, high deglycosylation levels are typically associated with endometriosis and form cloudy precipitates when LH levels of the biological body samples are low. In the period of LH surge for women without endometriosis, the low estradiol levels will result in decreased concentration of acidic glycoslylated proteins. Further, increased salt or ionic strength is also believed to contribute to self-aggregation of neutral glycosylated proteins which would normally not self-aggregate when ionic strength is decreased. In contrast, women with endometriosis are believed have a lower degree of protein aggregation with apatite, e.g., $(Ca_{10}(PO_4)_6(OH)_2$ during the LH surge because decreased estradiol production and no changes in ionic strength lead to diminished pathological impact of estradiol during the LH surge period.

By determining whether or not the female mammal had a LH surge at the time the biological sample (e.g., saliva) was obtained, it is possible to apply this diagnostic to test for all phases of the menstrual cycle and thereby screen for the presence of endometriosis in all women as long as the LH level is known. LH levels may be measured using over-the-counter products such as Clear Blue, NexCare or First Response available in drug stores or online purchasing. The diagnosis procedure may be deferred for about 48 hours or more if the LH level is considered at surge levels which are defined in the protocol of the commercially available LH test kit.

According to another exemplary embodiment of the invention, an endometriosis diagnostic method is provided on a biological sample obtained from a female mammal having had a menstrual period within 90 days of the biological sample having been obtained The biological sample obtained from the female mammal during the luteal phase of the menstrual cycle is subject to an in vitro diagnostic procedure in which the biological sample is contacted with an apatite compound, such as hydroxyapatite, a flavonol, and an anthocyanin for an effective time to produce a color response. Based on the color response, it is determined whether or not the female mammal has endometriosis. As described above in connection with the first exemplary embodiment, color responses may be determined within about 1 hour of conducting the assay. After approximately 1 hour, the color response may begin to fade. Similar concentrations of saliva and other conditions and parameters to those specified above with respect to the first embodiment may be used.

The exemplary method of this embodiment preferably is carried out on a female mammal having an active menstrual cycle, with the biological sample having been obtained during the luteal phase of the menstrual cycle. The female mammal preferably is within her child bearing years, is not pregnant, and is not post-menopause. Procurement of the biological sample during the luteal cycle phase may be determined by counting how many days have passed since menstruation. Alternatively, procurement of the biological sample during the luteal cycle phase may be determined based on whether or not the female mammal is past the day when LH surges as tested in a commercially available LH testing kit. The hydroxyapatite may be obtained from the same commercial sources as described above.

An exemplary flavonol suitable for this and other exemplary embodiments of the invention is quercetin. For example, according to one exemplary procedure, $1\times10^{-3}$ to $1\times10^{-4}$ molar concentration of quercetin is dissolved in ethanol mixed in a ratio by volume of 80:20, for ethanol mixed with a buffer at pH≥8. 40 microliters of this solution is added to the hydroxyapatite substrate and allowed to dry at ambient conditions. The test sample is inoculated onto the hydroxyapatite surface that has been treated with the flavonol. The resulting color is yellow whether or not the woman has endometriosis. In order to read a color response that is distinctive of whether or not the subject has endomestriosis, the assay is exposed to an anthocyanin pigment.

Generally, anthocyanin pigments useful for this embodiment may possess the following structure:

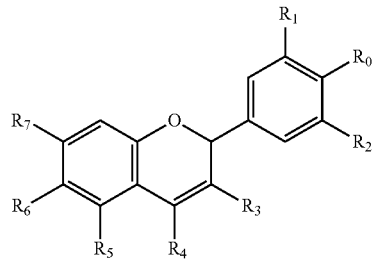

(Formula I)

wherein $R_0$ may be selected from the group consisting of hydrogen and hydroxy, but preferably is hydroxy; $R_1$ may be selected from the group consisting of hydrogen, hydroxy, and $C_1$-$C_4$ alkoxy such as methoxy; $R_2$ may be selected from the group consisting of hydrogen, hydroxy, and $C_1$-$C_4$ alkoxy such as methoxy; $R_3$ (appended to the three-position carbon) and $R_5$ (appended to the five-position carbon) each is an O-glycosyl group, wherein $R_3$ and $R_5$ may be the same or different relative to one another; $R_4$ is preferably hydrogen; $R_6$ may be selected from the group consisting of hydroxy and hydrogen; and $R_7$ is selected from the group consisting of hydrogen, hydroxy, and $C_1$-$C_4$ alkoxy, but preferably is a hydroxy group.

Representative exemplary anthocyanins pigments of this first exemplary embodiment include cyanidin 3,5-diglucoside, petunidin-3,5-diglucoside, hirsutidin 3,5-diglucoside, pelargonidin 3,5-diglucoside, malvidin 3,5-diglucoside, and petunidin 3,5-diglucoside. These and other anthocyanins and other flavonoids described herein may be obtained from various commercial sources, such as, for example, Sigma Aldrich and Polyphenols in Norway. Alternative sources are also available. The anthocyanin may be dissolved in methanol, for example, to a $1\times10^{-3}$ to $1\times10^{-4}$ molar concentration. Other alcohol solutions having molar concentrations of for example, $10^{-1}$ M to $5\times10^{-4}$ M are also suitable. Alternatively, the solution may be dried before it is deposited on the assay substrate. It is preferred that the test sample be first exposed to the hydroxyapatite and quercetin, and approximately 10 minutes pass before the anthocyanin is added to the sample. It is also preferred that the amount of quercetin and anthocyanin be approximately equal. The anthocyanin may be premixed in a solvent or the treated test sample may be allowed to flow onto a surface that holds the dried anthocyanin.

Exemplary embodiments of the invention will now be discussed in further detail in connection with the following examples, which are not necessarily limiting on or exhaustive representations of the scope of the invention.

EXAMPLES

Examples 1-82

60 microliter (ml) whole saliva samples from eighty-two (82) female humans having active menstrual cycles and experiencing pain or infertility were thawed. Each thawed sample was pipetted into a respective well of a substrate having an Osteo assay CLS 3988 (Corning, Inc.) embedded in the well surface. After at least 10 minutes, photographs were taken and determinations were made as to whether the samples in the wells were cloudy or clear. Cloudiness or turbidity versus clearness was determined based on whether or not newsprint could be read through the transparent well holding the treated biological sample. Alternatively, photographs producing one reflective spot were considered cloudy, whereas photographs having more than one reflective spot were considered clear.

Of the 82 females, a laparoscopy procedure performed on each female indicated 52 of the females had endometriosis and 30 females did not. The laparoscopy results were compared to the test results, and the following findings were made.

The comparison indicated that the laparoscopy procedure and test results corresponded for 35 of the 52 females having endometriosis; that is, 17 of the 52 females having endometriosis produced false negatives under the test procedure and 35 of the 52 females produced true positives. The test results were then screened for women having no menstrual cycle within 90 days of the biological sample having been obtained. 21 of the 52 females having endometriosis did not have a menstrual cycle within 90 days of testing. Of these 21 females not having a menstrual cycle, 7 produced false negatives and 14 produced true positives. Of the remaining 31 females having a menstrual cycle within 90 days of testing, 21 produced true positives and 10 produced false negatives for an accuracy of 67.7 percent.

If one considers only those women who cycled and had an ovulation phase; i.e., exclude the women on birth control pill who had a non-ovulatory cycle, then there are 21 women with laparoscopically diagnosed endometriosis with an ovulatory menstrual cycle. Of these 21 women, 2 had a LH surge and these 2 tested produced a false negative, that is, a clear response to the assay. Of the remaining 19 women laparoscopically diagnosed with endometriosis, results from 3 women showed false negative responses and 16 showed true positive (or cloudy responses), corresponding to an accuracy of 84 percent. Of the three women with laparoscopically diagnosed endometriosis who gave false negative results, all three had a diagnosis that was either considered mild or questionable.

The laparoscopy procedure and test results corresponded for 19 of the 30 females not having endometriosis; that is, 11 of the 30 females not having endometriosis produced false positives, while 19 of the 30 females not having endometriosis produced true negatives. The test results were then screened for women having no menstrual cycle within 90 days of the biological sample having been obtained. 9 of the 30 females not having endometriosis did not have a menstrual cycle within 90 days of testing. Of these 9 females not having a menstrual cycle within 90 days of testnig, 7 produced false positives and 2 produced true negatives. Of the remaining 21 females having a menstrual cycle within 90 days of testing, 17 produced true negatives and 4 produced false positives for an accuracy of 81 percent.

Examples 83-162

Examples 83-162 involved the application of quercetin to hydroxyapatite in a titer plate, then introduction of saliva samples for testing, followed by the addition of malvidin 3,5-diglucoside. The saliva samples taken from female subjects during their luteal phase were further processed by dissolving 20 microliters of $1 \times 10^{-3}$ M quercetin in ethanol and diluting with sodium hydroxide to a pH of 8. 20 microliters of $1 \times 10^{-3}$ M malvidin 3,5-diglucoside dissolved in methanol were then added to the well, and color was recorded using a digital camera. The following results were observed.

32 of 53 women with endometriosis (as determined by laparoscopy) had a menstrual cycle within 90 days of testing, of which 21 samples were from women with cycles and no birth control pill and 11 samples were from women who were taking birth control pill that had a menstrual cycle. Of the group of 21 women who were not on birth control pill and had a menstrual cycle, 12 of the 21 women were in the follicular phase and 9 of the 21 women were in the luteal phase. 5 of the women in the luteal phase gave positive results to the turbidity test and all five 5 had a blue color response to the flavonoid assay. 3 of 4 women who produced pink responses in the luteal phase also had negative results to the turbidity test. These 3 women were all classified as having either questionable endometriosis or endometriosis that was diagnosed as very mild according to the laparoscopy report.

There were 22 women with no endometriosis (as determined by laparoscopy) who had a menstrual cycle. 7 of these women were on the birth control pill, and 15 were not on birth control. 6 women were in the luteal phase and 5 of the 6 samples taken from the luteal phase produced no blue. The color response ranged from faded pink to pink and pink intensity correlated with the concentration of saliva estradiol. 10 women who did not have endometriosis showed a range of color responses in the follicular phase. Results from women who showed blue color correlated with the late follicular phase about 4-5 days before the period when ovulation would be expected.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. The specification describes specific examples to accomplish a more general goal that may be accomplished in another way.

Only those claims which use the words "means for" are to be interpreted under 35 USC 112, sixth paragraph. Moreover, no limitations from the specification are to be read into any claims, unless those limitations are expressly included in the claims.

What is claimed is:

1. An endometriosis screening method, comprising:
   contacting in vitro saliva with an apatite compound for an effective time to provide a responsive visual appearance, wherein the saliva is from a female mammal that experienced an ovulatory menstrual cycle within a period of 90 days leading up to a date on which the saliva was obtained, and further wherein the date on which the saliva was obtained within the 90-day period was not 24 to 36 hours before the female mammal experienced a luteinizing hormone surge consistent with ovulation; and
   observing the responsive visual appearance and providing a screening result as to whether the female mammal has endometriosis based on the responsive visual appearance, wherein the screening result is that the female mammal does not have endometriosis if the responsive visual appearance is clear and non-cloudy to an unaided human eye, and wherein the screening result is that the female mammal has endometriosis if the responsive visual appearance is cloudy to the unaided human eye.

2. The endometriosis screening method of claim 1, wherein the female mammal is human.

3. The endometriosis screening method of claim 1, wherein the apatite compound comprises hydroxyapatite.

4. The endometriosis screening method of claim 1, wherein the female mammal is human and the apatite compound comprises hydroxyapatite.

5. An endometriosis screening method, comprising contacting in vitro saliva obtained from a female mammal during the luteal phase of a menstrual cycle with an apatite compound, a flavonol pigment, and an anthocyanin pigment for an effective time to produce a color response, and providing a screening result as to whether the female mammal has endometriosis based on the color response, wherein the color response corresponding to the screening result is affected by the anthocyanin pigment.

6. The endometriosis screening method of claim 5, wherein the screening result is that the female mammal does not have endometriosis if the color response is pink, and wherein the screening result is that the female mammal has endometriosis if the color response is blue.

7. The endometriosis screening method of claim 5, wherein the female mammal is human.

8. The endometriosis screening method of claim 5, wherein the flavonol pigment comprises quercetin.

9. The endometriosis screening method of claim 5, wherein the anthocyanin pigment has a three-position carbon with a first O-glycosyl group and a five-position carbon with a second O-glycosyl group.

10. The endometriosis screening method of claim 5, wherein the anthocyanin pigment comprises a member selected from the group consisting of cyanidin 3,5-diglycoside, petunidin 3,5-diglycoside, hirsutidin 3,5-diglycoside, pelargonidin 3,5-diglycoside, and malvidin 3,5-diglycoside.

11. The endometriosis screening method of claim 5, wherein the apatite compound comprises hydroxyapatite.

12. The endometriosis screening method of claim 5, wherein the female mammal is human and wherein the apatite compound comprises hydroxyapatite.

13. An endometriosis screening method, comprising contacting in vitro saliva obtained from a female mammal during the luteal phase of a menstrual cycle with an apatite compound, quercetin, and malvidin 3,5-diglucoside for an effective time to produce a color response, and providing a screening result as to whether the female mammal has endometriosis based on the color response, wherein the screening result is that the female mammal does not have endometriosis if the color response is pink, and wherein the screening result is that the female mammal has endometriosis if the color response is blue.

14. The endometriosis screening of claim 13, wherein the female mammal is human.

15. The endometriosis screening method of claim 13, wherein the apatite compound comprises hydroxyapatite.

16. The endometriosis screening method of claim 13, wherein the female mammal is human and the apatite compound comprises hydroxyapatite.

* * * * *